United States Patent [19]
Kmiec et al.

[11] Patent Number: 5,942,386
[45] Date of Patent: Aug. 24, 1999

[54] ANTI-FUNGAL AGENTS AND METHODS OF IDENTIFYING AND USING THE SAME

[75] Inventors: Eric B. Kmiec, Malvern; David L. Gerhold, Huntingdon Valley; Allyson Cole Strauss, Philadelphia, all of Pa.

[73] Assignee: Thomas Jefferson University, Philadelphia, Pa.

[21] Appl. No.: 08/973,831

[22] PCT Filed: Jun. 7, 1996

[86] PCT No.: PCT/US96/09530

§ 371 Date: Mar. 23, 1998

§ 102(e) Date: Mar. 23, 1998

[87] PCT Pub. No.: WO96/40886

PCT Pub. Date: Dec. 19, 1996

Related U.S. Application Data

[63] Continuation of application No. 08/485,621, Jun. 7, 1995, Pat. No. 5,691,187
[60] Provisional application No. 60/000,399, Jun. 21, 1995.

[51] Int. Cl.⁶ .............................. C12Q 1/25; C12Q 1/68
[52] U.S. Cl. .................................. 435/4; 435/6; 435/7.4; 435/7.6
[58] Field of Search .......................... 435/4, 6, 7.4, 7.6, 435/255.1, 255.4, 254.2, 252.22, 254.21, 255.2, 252.3, 252.33, 325

[56] References Cited

U.S. PATENT DOCUMENTS

| | | | |
|---|---|---|---|
| 3,894,029 | 7/1975 | Winterfeldt et al. | 546/48 |
| 4,031,098 | 6/1977 | Sugasawa | 546/48 |
| 4,399,276 | 8/1983 | Miyasaka et al. | 544/361 |
| 4,399,282 | 8/1983 | Miyasaka et al. | 546/48 |
| 4,473,692 | 9/1984 | Miyasaka et al. | 546/48 |
| 4,513,138 | 4/1985 | Miyasaka et al. | 546/48 |
| 4,604,463 | 8/1986 | Miyasaka et al. | 544/125 |
| 4,736,866 | 4/1988 | Leder et al. | 800/10 |
| 4,873,191 | 10/1989 | Wagner et al. | 800/25 |
| 4,914,205 | 4/1990 | Sawada et al. | 546/70 |
| 4,939,255 | 7/1990 | Tagawa et al. | 540/578 |
| 4,981,968 | 1/1991 | Wall et al. | 544/361 |
| 5,004,758 | 4/1991 | Boehm et al. | 514/283 |
| 5,041,424 | 8/1991 | Saulnier et al. | 514/27 |
| 5,053,512 | 10/1991 | Wani et al. | 546/41 |
| 5,061,795 | 10/1991 | Tagawa et al. | 546/41 |
| 5,061,800 | 10/1991 | Yaegashi et al. | 546/48 |
| 5,106,742 | 4/1992 | Wall et al. | 435/233 |
| 5,122,606 | 6/1992 | Wani et al. | 546/41 |
| 5,155,225 | 10/1992 | Fortunak et al. | 546/70 |
| 5,162,532 | 11/1992 | Comins et al. | 546/48 |
| 5,180,722 | 1/1993 | Wall et al. | 514/219 |
| 5,212,317 | 5/1993 | Comins | 546/301 |
| 5,223,506 | 6/1993 | Luzzio | 514/279 |
| 5,244,903 | 9/1993 | Wall et al. | 514/279 |
| 5,342,947 | 8/1994 | Lackey et al. | 546/41 |
| 5,391,745 | 2/1995 | Danishefsky et al. | 546/48 |
| 5,395,939 | 3/1995 | Comins | 546/115 |
| 5,405,963 | 4/1995 | Fotunak et al. | 546/48 |
| 5,691,187 | 11/1997 | Kmiec et al. | 435/252.3 |

FOREIGN PATENT DOCUMENTS

WO96/40886  12/1996  WIPO.

OTHER PUBLICATIONS

Bjornsti, et al., "Expression of Human DNA Topoisomerase I in Yeast Cells Lacking Yeast DNA Topoisomerase I: Restoration of Sensitivity of the Cells to the Antitumor Drug Camptothecin", *Cancer Res.*, 1989, 49, 6318–6323.

Elble, R., "A Simple and Efficient Procedure for Transformation of Yeasts", *BioTechniques*, 1992, 13, 18–20.

Fostel, et al., "Characteristics of NDA Topoisomerase I from *Candida albicans* as a Target for Drug Discovery", *Antimicrobial Agents & Chemotherapy*, 1992, 36, 2131–2128.

Shen, et al., "DNA topoisomerase inhibitors as antifungal agents", *Advances in Pharmacol.*, 1994, 29B, 227–24.

Taylor, et al., "Identification of the gene encoding DNA topoisomerase I from *Candida albicans*", *Antimicrobial Agents & Chemotherapy*, 1992, 36, 2131–2128.

Thrash, et al., "Cloning, characterization, and sequence of the yeast DNA Topoisomerase I gene", *Proc. Natl. Acad. Sci. USA*, 1985, 82, 4374–4378.

Nitiss, et al., "DNA topoisomerase–targeting antitumor drugs can be studied in yeast", *Proc. Natl. Acad. Sci. USA*, 1988, 85, 7501–7505.

*Primary Examiner*—Robert A. Wax
*Assistant Examiner*—Gabriele E. Bugaisky
*Attorney, Agent, or Firm*—Woodcock Washburn Kurtz Mackiewicz & Norris LLP

[57] ABSTRACT

Substantially pure *C. albicans* topoisomerase I protein is disclosed. Nucleic acid molecules that encode *C. albicans* topoisomerase I protein, recombinant expression vectors that comprise a nucleic acid sequence that encodes *C. albicans* topoisomerase I protein, and host cells that comprise recombinant expression vectors that comprise nucleic acid sequences that encode *C. albicans* topoisomerase I protein are disclosed. Fragments of nucleic acid molecules with sequences encoding *C. albicans* topoisomerase I protein and oligonucleotide molecules that comprise a nucleotide sequence complementary to fragment of a nucleotide sequence that encodes *C. albicans* topoisomerase I protein are disclosed. Antibodies which bind to an epitope on *C. albicans* topoisomerase I protein are disclosed. Methods of identifying inhibitors of *C. albicans* topoisomerase I protein are disclosed. Camptothecin analogs useful as inhibitors of *C. albicans* topoisomerase I protein are disclosed and methods of using camptothecin analogs as inhibitors of *C. albicans* topoisomerase I protein are disclosed.

13 Claims, No Drawings

ANTI-FUNGAL AGENTS AND METHODS OF IDENTIFYING AND USING THE SAME

CROSS REFERENCE TO RELATED APPLICATION

This application is a 371 of PCT application PCT/US96/09530 filed Jun. 7, 1996, and a continuation of Ser. No. 08/485,621 filed Jun. 7, 1995, issued as U.S. Pat. No. 5,691,187 and a provisional application Ser. No. 60/000,399 filed Jun. 21, 1995.

FIELD OF THE INVENTION

The invention relates to the identification and cloning of the topoisomerase I gene (TOP1) from *Candida albicans* and the use of the gene in complementation assays to identify inhibitors of the *C. albicans* TOP1 while having no effect on the homologous human TOP1. The invention relates to compounds that selectively inhibit *C. albicans* TOP1 and the use of such compounds to kill fungi and in the treatment of individuals with fungal infections.

BACKGROUND OF THE INVENTION

*Candida albicans* is the most important fungal pathogen infecting humans. This fungal pathogen causes vaginal yeast infections, as well as oral infections and tissue invasion in immunocompromised patients. Oral infections are highly prevalent in AIDS patients and in cancer patients undergoing bone marrow replacement therapy. Only three types of anti-fungal drugs are currently approved for use in humans. Unfortunately, these anti-fungal drugs have serious side effects and have limited efficacy.

Yeast *Saccharomyces cerevisiae* strains that express DNA topoisomerase I and are permeable to the anti-tumor alkaloid camptothecin compounds are killed by the compound (Nitiss, et al., *Proc. Natl. Acad. Sci. USA*, 1988, 85, 7501–7505). Yeast strains which are permeable to camptothecin but lack topoisomerase I can establish sensitivity to camptothecin by expression of human DNA topoisomerase I (Bjornsti, et al., *Cancer Res.*, 1989, 49, 6318–6323). Thus, yeast cells lacking endogenous topoisomerase I are killed by camptothecin if they express human topoisomerase I. Camptothecin kills such yeast strains by stabilizing a covalent topoisomerase I-DNA conjugate which leaves a broken DNA strand. The broken single strand can be processed to a double-strand break during DNA replication. If this damage is not repaired by DNA recombination, it leads to cell death. Camptothecin, however, is not a candidate for human therapy for fungal-associated conditions due to its activity on human topoisomerase I.

There is a need for compounds which selectively inhibit *C. albicans* topoisomerase I activity but which do not inhibit human topoisomerase I activity. There is a need for kits and methods of identifying such compounds. There is a need for isolated *C. albicans* topoisomerase I protein, and for compositions and methods of producing and isolating *C. albicans* topoisomerase I protein. There is a need for methods of treating individuals that have fungal infections.

SUMMARY OF THE INVENTION

The present invention relates to substantially pure *C. albicans* topoisomerase I protein.

The present invention relates to substantially pure *C. albicans* topoisomerase I protein having the amino acid sequence of SEQ ID NO:2.

The present invention relates to nucleic acid molecules that encode *C. albicans* topoisomerase I protein.

The present invention relates to nucleic acid molecules encoding *C. albicans* topoisomerase I protein that consists of SEQ ID NO:1.

The present invention relates to recombinant expression vectors that comprise a nucleic acid sequence that encodes *C. albicans* topoisomerase I protein.

The present invention relates to host cells that comprise recombinant expression vectors that encode *C. albicans* topoisomerase I protein.

The present invention relates to fragments of nucleic acid molecules with sequences encoding *C. albicans* topoisomerase I protein that have at least 10 nucleotides.

The present invention relates to oligonucleotide molecules that comprise a nucleotide sequence complimentary to a nucleotide sequence of at least 10 nucleotides of SEQ ID NO:1.

The present invention relates to isolated antibodies which bind to an epitope on SEQ ID NO:2.

The present invention relates to host cells that have deficient or non-functional endogenous topoisomerase I proteins and comprise recombinant expression vectors that encode *C. albicans* topoisomerase I protein.

The present invention relates to methods of identifying inhibitors of *C. albicans* topoisomeerase I protein. The methods comprise contacting a first host cell which is deficient in a functional topoisomerase gene except for a functional gene that encodes *C. albicans* topoisomerase I protein with a test compound, contacting a second host cell which is deficient in a functional topoisomerase gene except for a functional gene that encodes non-*C. albicans* topoisomerase I protein with a test compound, and identifying a test compound whose presence results in the death of the first host cell but not the second host cell.

The present invention relates to compounds that are specific inhibitors of *C. albicans* topoisomerase I protein which selective inhibit *C. albicans* topoisomerase I protein. The compounds of the invention inhibit *C. albicans* topoisomerase I protein much greater than they inhibit human or other non-*C. albicans* topoisomerase I protein such that the compounds of the invention are lethal to *C. albicans* through the inhibition of activity of *C. albicans* topoisomerase I protein but that do not kill non-*C. albicans* species which come into contact with the compound.

The present invention relates to compounds that are Camptothecin analogs which selectively inhibit *C. albicans* topoisomerase I. Camptothecin analogs of the invention interact or otherwise interfere with the residues in the active site region of the *C. albicans* topoisomerase I, particularly the Methionine residue at Met736 which is present in *C. albicans* instead of the leucine located 2 residues amino-terminal to the active site tyrosine, Tyr738, found in human topoisomerase I.

The present invention relates to methods of treating individuals who have fungal infections comprising the step of administering to such individuals a therapeutically effective amount of a compound of the invention.

The present invention relates to methods of preventing fungal infections in individuals comprising the step of administering to such individuals a prophylactically effective amount of a compound of the invention.

DETAILED DESCRIPTION OF THE INVENTION

The present invention provides the cloned gene that encodes C. albicans topoisomerase I protein. The discovery of the C. albicans topoisomerase I gene and the protein that it encodes provides the means to design and discover specific inhibitors of C. albicans topoisomerase I protein.

As used herein the terms "specific inhibitor of C. albicans topoisomerase I protein" and "selective inhibitor of C. albicans topoisomerase I protein" are used interchangeably and are meant to refer to compounds that result in the death of C. albicans through the inhibition of activity of C. albicans topoisomerase I protein but that do not kill non-C. albicans species which come into contact with the compound. Compounds that selectively inhibit C. albicans topoisomerase I activity are those which inhibit C. albicans topoisomerase I activity but not the activity of non-C. albicans topoisomerase I proteins.

According to one aspect of the present invention, the gene that encodes C. albicans topoisomerase I protein may be used to produce recombinant microorganisms that are useful to screen compounds for specific inhibitors. A host organism deficient in endogenous topoisomerase I protein may be "complemented" with C. albicans topoisomerase I, i.e. furnished with a functional copy of the C. albicans topoisomerase I gene or cDNA. Expression of the nucleotide sequence that encodes C. albicans topoisomerase I protein results in production of functional protein which functions in place of the missing or non-functional endogenous topoisomerase I. Comparative studies can be performed to evaluate the effect test compounds have on the hosts that are complemented with C. albicans topoisomerase I compared to the effect the same test compounds have on the hosts with functional endogenous topoisomerase I or hosts that are complemented with non-C. albicans topoisomerase I. In some preferred embodiments, inhibitors are identified using complementation assays in which a first host cell that expresses C. albicans topoisomerase I protein to survive is contacted with a test compound and a second host cell which expresses a non-C. albicans topoisomerase I protein to survive is contacted with the same test compound. If the first host cell dies in the presence of the test compound but the second host cell lives in the presence of the same test compound, the compound is indicated to be an inhibitor of C. albicans topoisomerase I protein.

Complemented host cells are deficient for functional endogenous topoisomerase I and rely on the activity of "foreign" topoisomerase I for survival. Host cells that are deficient for functional endogenous topoisomerase I and which can be complemented by "foreign" topoisomerase I for survival include yeasts, Saccharomyces species, Schizosaccharomyces species, *Escherichia coli*, and *Salmonella typhimurium*. In some preferred embodiments, complemented host cells are yeasts. In some preferred embodiments, complemented host cells are yeast: strain L1242, which is described in Thrash, et al., *Proc. Natl. Acad. Sci. USA*, 1985, 82, 4374–4378, which is disclosed in its entirety herein by reference, or other top1⁻ yeast strains.

Expression of human TOP1 in yeast is described in Bjornsti, et al., *Cancer Res.*, 1989, 49, 6318–6323, which is disclosed in its entirety herein by reference. Bjornsti, et al., describe the complementation of conditional lethal human topoisomerase I mutant. In a similar manner, yeasts and the like can be transformed with nucleic acid molecules encoding C. albicans topoisomerase I protein that consists of SEQ ID NO:2. Accordingly, complementation can be performed with yeasts transformed with nucleic acid molecules encoding C. albicans topoisomerase I protein that consists of SEQ ID NO:2.

The methods of the invention are useful to identify selective inhibitors of C. albicans topoisomerase I protein. Inhibitors are useful as anti-fungal agents, specifically anti-C. albicans agents. Kits are provided for screening compounds for identifying selective inhibitors of C. albicans topoisomerase I protein.

The nucleotide sequence that encodes C. albicans topoisomerase I protein and that is disclosed herein as SEQ ID NO:1 allows for the production of complemented host cells which survive due to the presence of functional C. albicans topoisomerase I protein. In preparing gene constructs for complementation of deficient hosts, SEQ ID NO:1 is introduced into a host and expressed. SEQ ID NO:1 may be inserted into an expression vector in which the coding sequence is operably linked to regulatory elements required for gene expression in the host. In some preferred embodiments the expression vector is pBM272, which allows regulated expression from the GAL1 promoter of *Saccharomyces cerevisiae*. The wild-type C. albicans TOP1 coding sequence can be inserted into the BamHI and HindIII sites of pBM272. As controls, deficient host cells may be complemented with human topoisomerase I or another topoisomerase I.

The nucleotide sequence that encodes C. albicans topoisomerase I protein and that is disclosed herein as SEQ ID NO:1 allows for the production of pure C. albicans topoisomerase I protein and the design of probes which specifically hybridize to nucleic acid molecules that encode C. albicans topoisomerase I protein and antisense compounds to inhibit transcription of the gene that encodes C. albicans topoisomerase I protein.

The present invention provides substantially purified C. albicans topoisomerase I protein. The present invention provides substantially purified C. albicans topoisomerase I protein which has the amino acid sequence consisting of SEQ ID NO:2. C. albicans topoisomerase I protein can be isolated from natural sources or produced by recombinant DNA methods.

The C. albicans topoisomerase I protein sequence differs substantially from the human topoisomerase I sequence. Such differences may be used to predict which compounds might show specific binding or inhibition of the C. albicans topoisomerase I. In particular, the active site region of the C. albicans topoisomerase I has a methionine residue, Met736, instead of the leucine/isoleucine located 2 residues amino-terminal to the active site tyrosine, Tyr738, found in human and other eukaryotic topoisomerase I proteins. Antibodies may be generated and selected which specifically bind to C. albicans topoisomerase I at an epitope which includes the methionine within the active site.

Antibodies that specifically bind to C. albicans topoisomerase I protein are provided. Such ancibodies are specific inhibitors of C. albicans topoisomerase I protein and may be used in methods of isolating pure C. albicans topoisomerase I protein and methods of inhibiting C. albicans topoisomerase I protein activity.

The antibodies may be used to purify the protein from natural sources using well known techniques and readily available starting materials. Such antibodies may also be used to purify C. albicans topoisomerase I protein from material present when producing the protein by recombinant DNA methodology. The present invention relates to antibodies that bind to an epitope which is specific for C.

*albicans* topoisomerase I protein as compared to human topoisomerase I protein. This epitope appears at amino acids 730 to 740 of SEQ ID NO:2.

As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies. The antibodies specifically bind to an epitope on SEQ ID NO:2. In some preferred embodiments, that epitope appears at amino acids 730 to 740 of SEQ ID NO:2. Antibodies that bind to an epitope on SEQ ID NO:2, particularly at amino acids 730 to 740 of SEQ ID NO:2 are useful to isolate and purify *C. albicans* topoisomerase I protein from both natural sources or recombinant expression systems using well known techniques such as affinity chromatography. Such antibodies are useful to detect the presence of such protein in a sample and to determine if cells are expressing the protein.

The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y., which is incorporated herein by reference. Briefly, for example, the *C. albicans* topoisomerase I protein, or an immunogenic fragment thereof is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to *C. albicans* topoisomerase I protein, the hybridoma which produces them is cultured to produce a continuous supply of antibodies.

Using standard techniques and readily available starting materials, a nucleic acid molecule that encodes *C. albicans* topoisomerase I protein may be isolated from a cDNA library, using probes which are designed using the nucleotide sequence information disclosed in SEQ ID NO:1. The present invention relates to an isolated nucleic acid molecule that comprises a nucleotide sequence that encodes *C. albicans* topoisomerase I protein and that comprises the amino acid sequence of SEQ ID NO:2. In some embodiments, the nucleic acid molecules consist of a nucleotide sequence that encodes *C. albicans* topoisomerase I protein. In some embodiments, the nucleic acid molecules comprise the nucleotide sequence that consists of the coding sequence in SEQ ID NO:1. In some embodiments, the nucleic acid molecules consist of the nucleotide sequence set forth in SEQ ID NO:1. The isolated nucleic acid molecules of the invention are useful to prepare constructs and recombinant expression systems for preparing isolated *C. albicans* topoisomerase I protein.

A genomic or cDNA library may be generated by well known techniques. Clones are identified using probes that comprise at least a portion of the nucleotide sequence disclosed in SEQ ID NO:1. The probes have at least 16 nucleotides, preferably 24 nucleotides. The probes are used to screen the genomic or cDNA libraries using standard hybridization techniques. In addition, the probes of the invention may be used to identify topoisomerase I genes from related organisms such as *Aspergillus fumigatus* and Cryptosporidium species.

The present invention relates to isolated nucleic acid molecules that comprise a nucleotide sequence identical or complementary to a fragment of SEQ ID NO:1 which is at least 10 nucleotides. In some embodiments, the isolated nucleic acid molecules consist of a nucleotide sequence identical or complementary to a fragment of SEQ ID NO:1 which is at least 10 nucleotides. In some embodiments, the isolated nucleic acid molecules comprise or consist of a nucleotide sequence identical or complementary to a fragment of SEQ ID NO:1 which is 15–150 nucleotides. In some embodiments, the isolated nucleic acid molecules comprise or consist of a nucleotide sequence identical or complementary to a fragment of SEQ ID NO:1 which is 15–30 nucleotides.

Isolated nucleic acid molecules that comprise or consist of a nucleotide sequence identical or complementary to a fragment of SEQ ID NO:1 which is at least 10 nucleotides are useful as probes for identifying genes and cDNA sequences that encodes *C. albicans* topoisomerase I protein, PCR primers for amplifying genes and cDNA that encodes *C. albicans* topoisomerase I protein, and antisense molecules for inhibiting transcription and translation of genes and cDNA, respectively, which encode *C. albicans* topoisomerase I protein.

The nucleotide sequence in SEQ ID NO:1 may be used to design probes, primers and complimentary molecules which specifically hybridize to the unique nucleotide sequences of *C. albicans* topoisomerase I protein. Probes, primers and complimentary molecules which specifically hybridize to nucleotide sequence that encodes *C. albicans* topoisomerase I protein may be designed routinely by those having ordinary skill in the art.

The present invention also includes labeled oligonucleotides which are useful as probes for performing oligonucleotide hybridization methods to identify clones that encode *C. albicans* topoisomerase I protein. Accordingly, the present invention includes probes that can be labelled and hybridized to unique nucleotide sequences of nucleic acid molecules that encode *C. albicans* topoisomerase I protein. The labelled probes of the present invention are labelled with radiolabeled nucleotides or are otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of nucleic acid molecules that encode *C. albicans* topoisomerase I protein.

PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990), which is incorporated herein by reference. Applications of PCR technology are disclosed in "Polymerase Chain Reaction" Erlich, H. A., et al., Eds. Cold Spring Harbor Press, Cold Spring Harbor, N.Y. (1989), which is incorporated herein by reference. Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 base pairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

One having ordinary skill in the art can isolate the nucleic acid molecule that encodes C. albicans topoisomerase I protein and insert it into an expression vector using standard techniques and readily available starting materials. The present invention relates to a recombinant expression vector that comprises a nucleotide sequence that encodes C. albicans topoisomerase I protein that comprises the amino acid sequence of SEQ ID NO:2. As used herein, the term "recombinant expression vector" is meant to refer to a plasmid, phage, viral particle or other vector which, when introduced into an appropriate host, contains the necessary genetic elements to direct expression of the coding sequence that encodes the C. albicans topoisomerase I protein. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. In some embodiments, the recombinant expression vector comprises the nucleotide sequence set forth in SEQ ID NO:1. The recombinant expression vectors of the invention are useful for transforming hosts to prepare recombinant expression systems for preparing the C. albicans topoisomerase I protein.

The present invention relates to a host cell that comprises the recombinant expression vector that includes a nucleotide sequence that encodes C. albicans topoisomerase I protein that comprises SEQ ID NO:2. In some embodiments, the host cell comprises a recombinant expression vector that comprises SEQ ID NO:1. Host cells for use in well known recombinant expression systems for production of proteins are well known and readily available. Examples of host cells include bacteria cells such as E. coli, yeast cells such as S. cerevisiae, insect cells such as S. frugiperda, non-human mammalian tissue culture cells chinese hamster ovary (CHO) cells and human tissue culture cells such as HeLa cells.

The present invention relates to a transgenic, non-human mammal that comprises the recombinant expression vector that comprises a nucleic acid sequence that encodes the C. albicans topoisomerase I protein that comprises the amino acid sequence of SEQ ID NO:2. Transgenic, non-human mammals useful to produce recombinant proteins are well known as are the expression vectors necessary and the techniques for generating transgenic animals. Generally, the transgenic animal comprises a recombinant expression vector in which the nucleotide sequence that encodes C. albicans topoisomerase I protein operably linked to a mammary cell specific promoter whereby the coding sequence is only expressed in mammary cells and the recombinant protein so expressed is recovered from the animal's milk:. In some embodiments, the coding sequence that encodes C. albicans topoisomerase 1 protein is SEQ ID NO:1.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production of C. albicans topoisomerase I in E. coli. The commercially available plasmid pYES2 (Invitrogen, San Diego, Calif.) may, for example, be used for production in S. cerevisiae strains of yeast. The commercially available MAXBAC™ complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as CHO cells. One having ordinary skill in the art can use these commercial expression vectors and systems or others to produce C. albicans topoisomerase I protein using routine techniques and readily available starting materials. (See e.g., Sambrook et al., Molecular Cloning a Laboratory Manual, Second Ed. Cold Spring Harbor Press (1989), which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., Molecular Cloning a Laboratory Manual, Second Ed. Cold Spring Harbor Press (1989).

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ions.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes C. albicans topoisomerase I protein is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate *C. albicans* topoisomerase I protein that is produced using such expression systems. The methods of purifying *C. albicans* topoisomerase I protein from natural sources using antibodies which specifically bind to *C. albicans* topoisomerase I protein as described above, may be equally applied to purifying *C. albicans* topoisomerase I protein produced by recombinant DNA methodology.

Examples of genetic constructs include the *C. albicans* topoisomerase I protein coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes *C. albicans* topoisomerase I protein from readily available starting materials. Such gene constructs are useful for the production of *C. albicans* topoisomerase I protein.

In some embodiments of the invention, transgenic non-human animals are generated. The transgenic animals according to the invention contain SEQ ID NO:1 under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce the *C. albicans* topoisomerase I protein. Preferred animals are rodents, particularly goats, rats and mice.

In addition to producing these proteins by recombinant techniques, automated peptide synthesizers may also be employed to produce *C. albicans* topoisomerase I protein. Such techniques are well known to those having ordinary skill in the art and are useful if derivatives which have substitutions not provided for in DNA-encoded protein production.

To screen compounds according to the methods of the present invention, at least two groups of host cells are tested. One host cell is complemented with functional *C. albicans* topoisomerase I. The other host cell either contains a functional endogenous topoisomerase I or is complemented with a non-*C. albicans* topoisomerase, preferably human topoisomerase. The groups are contacted with test compounds and the survivability of each of the two groups is observed. If a test compound leads to the death of the host cells complemented with *C. albicans* topoisomerase I but not those with non-*C. albicans* topoisomerase I, the compound is a selective inhibitor of *C. albicans* topoisomerase I.

In some embodiments of the invention, the preferred concentration of test compound is between 1 $\mu$M and 500 $\mu$M. A preferred concentration is 10 $\mu$M to 100 $\mu$M. In some preferred embodiments, it is desirable to use a series of dilutions of test compounds.

Kits are included which comprise containers with host cells or reagents necessary to produce host cells and/or screen test compounds. In additions, kits comprise instructions for performing such methods.

Another aspect of the present invention relates to camptothecin analogs that selectively inhibit *C. albicans* topoisomerase I protein, but not human topoisomerase I. According to the present invention, such compounds may be administered to individuals identified as suffering from fungal infections to kill the infecting organism.

Camptothecin analogs which selectively inhibit *C. albicans* topoisomerase I protein may be identified using the assay of the present invention. The host organism deficient in endogenous topoisomerase I protein is complemented with *C. albicans* topoisomerase I and comparative studies are performed to evaluate the effect that camptothecin analogs have on the hosts that are complemented with *C. albicans* topoisomerase I compared to the effect the same camptothecin analog has on the hosts with functional endogenous topoisomerase I or hosts that are complemented with non-*C. albicans* topoisomerase I. In some preferred, camptothecin analogs that selectively inhibit *C. albicans* topoisomerase I are identified using complementation assays in which a first host cell that expresses *C. albicans* topoisomerase I protein to survive is contacted with a camptothecin analog and a second host cell which expresses a non-*C. albicans* topoisomerase I protein to survive is contacted with the same camptothecin analog. If the first host cell dies in the presence of the camptothecin analog but the second host cell lives in the presence of the same camptothecin analog, the camptothecin analog is indicated to be a selective inhibitor of *C. albicans* topoisomerase I protein.

The assay of the invention is useful to identify camptothecin analogs that are selective inhibitors of *C. albicans* topoisomerase I protein. The camptothecin analogs that are selective inhibitors are useful as anti-fungal agents, specifically anti-*C. albicans* agents.

In some embodiments, compounds of the invention interact with Met736.

The invention relates to camptothecin analogs that are selective inhibitors of *C. albicans* topoisomerase I. Camptothecin analogs that are selective inhibitors of *C. albicans* topoisomerase I may be identified by screening camptothecin analogs disclosed in U.S. Pat. Nos. 5,405,963; 5,401,747; 5,395,939; 5,391,745; 5,364,858; 5,342,947; 5,244,903; 5,227,380; 5,223,506; 5,212,317; 5,200,524; 5,191,082; 5,180,722; 5,162,532; 5,155,225; 5,122,606; 5,122,526; 5,106,742; 5,061,800; 5,061,795; 5,053,512; 5,041,424; 5,004,758; 4,981,968; 4,939,255; 4,914,205; 4,604,463; 4,545,880; 4,513,138; 4,473,692; 4,399,282; 4,399,276; 4,031,098; and 3,894,029; which are each incorporated herein by reference. The present invention relates to camptothecin analogs disclosed in the patents which are inhibitors of *C. albicans*.

In some embodiments of the invention, the preferred concentration of camptothecin analogs is between 1 $\mu$M and 500 $\mu$M. A preferred concentration is 10 $\mu$M to 100 $\mu$M. In some preferred embodiments, it is desirable to use a. series of dilutions of test compounds.

The present invention relates to methods of inhibiting *C. albicans* topoisomerase I activity which comprises contacting *C. albicans* topoisomerase I with an effective amount of a camptothecin analog with selective inhibitory activity, or its pharmaceutically acceptable salt. Camptothecin analogs that are *C. albicans* topoisomerase I inhibitors are useful as antifungal compounds. The present invention relates to methods of treating an animal suffering from a fungal infection by administering an amount of a *C. albicans* topoisomerase I with an effective amount of a camptothecin analog or analogs with selective inhibitory activity, or its pharmaceutically acceptable salt, effective to inhibit *C. albicans* topoisomerase I activity.

The method that is the present invention is useful in the treatment of diseases which involve funga infections such as opportunistic infections in immunocomprornised patients such as those suffering from HIV infection including those having AIDS. In addition, the methods are useful for treating vaginal yeast infections. Accordingly, the present invention relates to a method of treating a mammal suffering from a fungal infection that comprises administering to the mammal, a therapeutically effective amount of a camptothecin analog with selective inhibitory activity, or its pharmaceutically acceptable salt which inhibits C. albicans topoisomerase I. Therapeutically effective amounts of compounds used in the method that is the present invention can be formulated as pharmaceutical preparations and administered to mammals who are suffering from fungal infections in order to counter the infection.

The method that is the present invention is useful in the prevention of fungal infections such as opportunistic infections in immunocompromised patients such as those suffering from HIV infection including those having AIDS. In addition, the methods are useful for treating vaginal yeast infections. Accordingly, the present invention relates to a method of administering a prophylactically effective amount of a camptothecin analog with selective inhibitory activity, or its pharmaceutically acceptable salt which inhibits C. albicans topoisomerase I to a mammal susceptible to fungal infection. Individuals susceptible to fungal infections include immunocompromised individuals prone to opportunistic infections such as individuals suffering from HIV infection including those with AIDS or patients undergoing intensive radiation and/or chemotherapies that result in an reduction in the resistance to infection, or women undergoing therapy that includes antibiotics. A prophylactically effective dose is one in which the incidence of fungal infection is decreased upon administration of such a dose compared to the incidence of fungal infection which would occur in the absence of such a dose.

Pharmaceutically acceptable salts of these compounds may be used in practicing the methods that are the present invention. Pharmaceutical compositions containing the compounds or salts may also be used in practicing the methods that are the present invention. Pharmaceutically acceptable salts useful in the methods of that are the invention include sodium, potassium, calcium, zinc, lithium, magnesium, aluminum, diethanolamine, tromethamine, ethylenediamine, meglumine, hydrochloric, hydrobromic or acetic acid.

The present invention relates to a method of using a camptothecin analog with selective inhibitory activity, or its pharmaceutically acceptable salt which inhibits C. albicans topoisomerase I to inhibit the activity of C. albicans topoisomerase I in cells. The range of amounts of camptothecin analog with selective inhibitory activity, or its pharmaceutically acceptable salt that a cell can be exposed to and be effective for inhibiting C. albicans topoisomerase I can be determined by one having ordinary skill in the art.

By inhibiting C. albicans topoisomerase I activity, the method that is the present invention is useful in the treatment and/or prevention of fungal infections.

The mode of administration of compounds and pharmaceutical compositions according to the methods that are the invention includes any means that produces contact of the active ingredient with the infectious organism in the body of a mammal or in a body fluid or tissue. These modes of administration include but not limited to oral, topical, hypodermal, intravenous, intramuscular and intraparenteral methods of administration. In practicing the methods that are the invention, the compounds may be administered singly or in combination with other compounds used in the methods of the invention, other pharmaceutical compounds, or in conjunction with therapies. In the methods of the invention, the compounds are preferably administered with a pharmaceutically acceptable carrier selected on the basis of the selected route of administration and standard pharmaceutical practice. One camptothecin analog or a plurality of camptothecin analogs in combination may be administered.

The methods may include administration of compounds to mammals, preferably humans, in therapeutically effective amounts which are effective to inhibit C. albicans topoisomerase I and kill C. albicans. The dosage administered in any particular instance will depend upon factors such as the pharmacodynamic characteristics of the compound of the invention, its mode and route of administration; age, health, and weight of the recipient; nature and extent of symptoms; kind of concurrent treatment, frequency of treatment, and the effect desired.

It is contemplated that the daily dosage of a compound used in the methods of the invention will be in the range of from about 1 $\mu$g to about 100 mg per kg of body weight, preferably from about 1 $\mu$g to about 40 mg per kg body weight, more preferably from about 10 $\mu$g to about 20 mg per kg per day, and most preferably 10 $\mu$g to about 1 mg per kg per day. Pharmaceutical compositions may be administered in a single dosage, divided dosages or in sustained release. Persons of ordinary skill will be able to determine dosage forms and amounts with only routine experimentation based upon the considerations of this invention. Isomers of the compounds and pharmaceutical compositions, particularly optically active stereoisomers, are also within the scope of the present invention.

Compounds may be administered as pharmaceutical compositions orally in solid dosage forms, such as capsules, tablets, and powders, or in liquid dosage forms, such as elixirs, syrups, and suspensions. The compounds may also be administered parenterally in sterile liquid dosage forms or topically in a carrier. The compounds may be formulated into dosage forms according to standard practices in the field of pharmaceutical preparations. See *Remington's Pharmaceutical Sciences*, A. Osol, Mack Publishing Company, Easton, Pa.

Compounds may be mixed with powdered carriers, such as lactose, sucrose, mannitol, starch, cellulose derivatives, magnesium stearate, and stearic acid for insertion into gelatin capsules, or for forming into tablets. Both tablets and capsules may be manufactured as sustained release products for continuous release of medication over a period of hours. Compressed tablets can be sugar or film coated to mask any unpleasant taste and protect the tablet from the atmosphere or enteric coated for selective disintegration in the gastrointestinal tract.

Liquid dosage forms for oral administration may contain coloring and flavoring to increase patient acceptance, in addition to a pharmaceutically acceptable diluent such as water, buffer or saline solution.

For parenteral administration, a compound may be mixed with a suitable carrier or diluent such as water, a oil, saline solution, aqueous dextrose (glucose), and related sugar solutions, and glycols such as propylene glycol or polyethylene glycols. Solutions for parenteral administration contain preferably a water soluble salt of the compound. Stabilizing agents, antioxidizing agents and preservatives may also be added. Suitable antioxidizing agents include sodium bisulfite, sodium sulfite, and ascorbic acid, citric acid and its salts, and sodium EDTA. Suitable preservatives include benzalkonium chloride, methyl- or propyl-paraben, and chlorbutanol.

EXAMPLES

Example 1

The topoisomerase I gene (TOP1) from *Candida albicans* is highly expressed in a yeast (*Saccharomyces cerevisiae*) strain lacking its native yeast TOP1 gene. The human TOP1 gene is highly expressed in a second top1-yeast strain. These two yeast strains are used to screen chemical compounds to find compounds which kill or inhibit the yeast expressing *C. albicans* TOP1 but not the yeast expressing the human TOP1.

*C. albicans* TOP1 was cloned using PCR. The PCR fragment was used as a probe to select a full-length TOP1 clone. The DNA sequence of the *C. albicans* TOP1 gene was determined and used to predict the topoisomerase I peptide sequence. The gene was excised from the DNA library vector using restriction enzymes, modified at the start of the protein-coding sequence, and ligated into a yeast expression plasmid. This plasmid is transformed into a top1⁻ yeast strain.

The *C. albicans* topoisomerase I protein sequence differs substantially from the human topoisomerase I sequence. Such differences may be used to predict which compounds might show specific binding or inhibition of the *C. albicans* topoisomerase I. In particular, the active site region has a methionine residue in place of the usual leucine/isoleucine located 2 residues amino-terminal to the active site tyrosine. Drugs may be selected based on ability to interact with this methionine residue.

It has been shown previously that overexpression of a TOP1 gene from another organism sensitizes a host yeast strain to camptothecin. Camptothecin kills such yeast strains by stabilizing a covalent topoisomerase I-DNA conjugate which leaves a broken DNA strand. The broken single strand can be processed to a double-strand break during DNA replication. If this damage is not repaired by DNA recombination, it leads to cell death.

The fastest ways to screen chemical or natural compounds or extracts, such as camptothecin analogs, for activity against *C. albicans* topoisomerase I is an adaption of the "zone of inhibition" assay for antibiotics. Two yeast strains, one expressing *C. albicans* topoisomerase I and the other strain expressing human topoisomerase I, are spread into a lawn of cells on minimal medium in 2 petri-dishes. Duplicate small paper discs are soaked in solutions of chemicals or natural products, and transferred to the surfaces of each of the 2 petri dishes. After 2–4 days at 30°, a thick lawn of yeast cells will grow on the petri-dishes. A compound, such as an active camptothecin analog, which produces a clear "zone of inhibition" of growth on the *C. albicans* TOP1 dish, but not the human TOP1 dish, is a specific inhibitor of *C. albicans* topoisomerase I.

In another embodiment of the assay, the two yeast strains, one expressing *C. albicans* topoisomerase I and the other expressing human topoisomerase I, are grown in liquid medium containing a possible inhibitory agent. A compound that inhibits the growth of *C. albicans* TOP1 yeast strain, but not the human TOP1 yeast strain, is a specific inhibitor of the *C. albicans* topoisomerase I.

Example 2
Yeast Transformation

The plasmid pBM-CaTOP1, and a similar plasmid expressing the human TOP1 gene, can be transformed into a top1⁻ *S. cerevisiae* strain by standard techniques, such as those described in Elble, R., *Biotechniques*, 1992, 13 (1), 78–80, which is disclosed in its entirety herein by reference. The plasmid can be selected by growing the yeast strain in minimal medium lacking uracil. The URA3 gene within pBM-CaTOP1 will enable the yeast strain to grow on medium lacking uracil. The expression of *C. albicans* topoisomerase I in *S. cerevisiae* can be verified by assaying the ability of a crude extract of this yeast strain to remove plasmid DNA supercoils as detailed in Thrash, et al., *Proc. Natl. Acad. Sci. USA*, 1985, 82, 4374–4378, which is disclosed in its entirety herein by reference.

Cloning *C. albicans* TOP1 Gene Into Expression Vector pBM272

The native genomic *C. albicans* TOP1 clone pCaT1-R12 constitutes a 3.4 kb EcoRI-EcoRI fragment containing the entire TOP1 gene, ligated into the pBC SK(–) plasmid (Stratagene, La Jolla, Calif.). This gene was modified by introducing a BamHI restriction site immediately 5' upstream of the coding sequence using standard techniques (Sambrook, et al., *Molecular Cloning a Laboratory Manual*, Second Ed. Cold Spring Harbor Press (1989)). The entire gene coding sequence was excised as a 2.4 kb BamHI-HindIII DNA fragment, and ligated into the BamHI-HindIII sites of yeast expression vector pBM272 using standard techniques. This plasmid, pBM-CaTOP1, can be introduced into top1⁻ yeast strain L1242 (*S. cerevisiae*; Thrash, et al., *Proc. Natl. Acad. Sci. USA*, 1985, 82, 4374–4378) or a derivative strain, K2979, provided by Dr. Ralph Keil, Hershey Medical Center, Hershey, Pa.). The K2979 genotype is: MATa HindIII(top1::LEU2) his4-260 ade2-1 ura3-52 leu2-3,112 trp1-HIII can1$^R$ lys2ΔBX::CAN1::LYS2 rDNA::URA3 rDNA::ADE2.

The cloned genomic *C. albicans* TOP1 gene can also be used to generate a top1⁻/top1⁻ *C. albicans* strain using the gene for gene disruption using standard techniques known to fungal geneticists.

Example 3

Camptothecin analogs may have the formula:

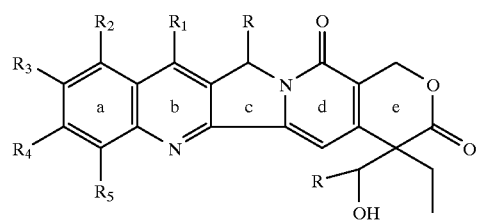

wherein:
R is a lower alkyl;
$R_1$ is H, lower alkyl, lower alkoxy, or halo; and
$R_2$, $R_3$, $R_4$ and $R_5$ may each independently be H, amino hydroxy, lower alkyl, lower alkoxy, lower alkylthio, di(lower alkyl)amino, cyano, methylenedioxy, Formyl, nitro, halo, trifluoromethyl, aminomethyl, azido, amido, hydrazino, or any of the standard twenty amino acids bonded to the A ring via the amino-nitrogen atom.

The synthesis of camptothecin analogs with this formula can be carried out by those having ordinary skill in the art using synthesis schemes such as those that are described in U.S. Pat. Nos. 5,212,317, 5,191,082, 5,395,939, 5,162,532, and 5,200,524.

Example 4

Camptothecin analogs may have the formula:

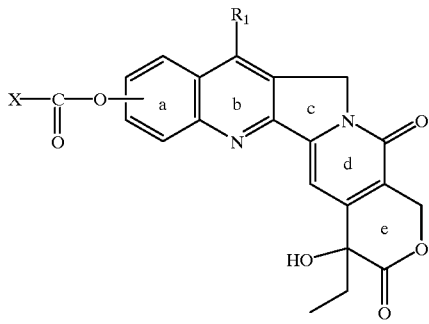

wherein:
$R_1$ is H, halo, or an alkyl group with 1–4 carbons; and
X is a chlorine atom or —$NR_2R_3$ where $R_2$ and $R_3$ are the same or different and each represents a hydrogen, a substituted or unsubstituted alkyl group with 1–4 carbons, or a substituted or unsubstituted carbocyclic or heterocyclic group.

The synthesis of Camptothecin analogs with this formula can be carried out by those having ordinary skill in the art using synthesis schemes such as those that are described in U.S. Pat. No. 4,604,463.

Example 5

Camptothecin analogs may have the formula:

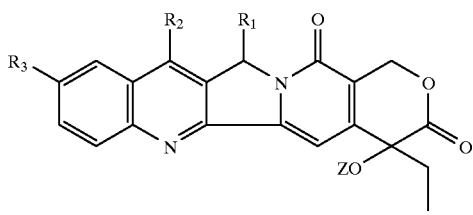

wherein:
$R_1$ is H, alkyl, hydroxyl, $CH_2OH$, COOH, aralkyl, alkoxy, acyloxy, $CH_2OR_4$, $COOR_5$ wherein $R_4$ is an alkyl or acyl group and $R_5$ is a lower alkyl or acyl group;
$R_2$ is H, alkyl, aralkyl, hydroxymethyl, carboxymethyl, acyloxymethyl, —CHO, —$CH_2OR'$, —CH(OR')$_2$ or —CH=N—X where R' is a lower alkyl group with 1–6 carbons or a phenylalkyl group with 1–3 carbon in the alkylene moiety thereof and X is hydroxyl or —$NR_6R_7$ where $R_6$ and $R_7$ are the same or different and each represents a hydrogen, or an alkyl group with 1–6 carbons, or when $R_6$ is hydrogen, $R_7$ may be an alkyl group with 1–6 carbons, a substituted or unsubstituted aryl group, a carbamoyl group, an acyl group, an aminoalkyl group or an amido group or when $R_6$ is a lower alkyl group $R_7$ may be an aminoalkyl group or $R_6$ and $R_7$ may be combined together with a nitrogen to form a heterocycle or quaternary salt thereof;
$R_3$ is the grouping —XR' where R' is H, alkyl, or acyl and X is oxygen or sulphur, a nitro group, an amino group, an alkylamino group, an acylamino group, or a halogen; and Z is hydrogen or an acyl group.

The synthesis of camptothecin analogs with this formula can be carried out by those having ordinary skill in the art using synthesis schemes such as those that are described in U.S. Pat. Nos. 4,473,692, 4,545,880, 4,399,276, 4,399,282.

Example 6

Camptothecin analogs may be camptothecirl oxide derivatives which have the formula as shown in Example 5 except that the Nitrogen on ring b is substituted with an oxygen.

The synthesis of camptothecin oxide derivatives with this formula can be carried out by those having ordinary skill in the art using synthesis schemes such as those that are described in U.S. Pat. No. 4,513,138.

Example 7

Camptothecin analogs may have the formula:

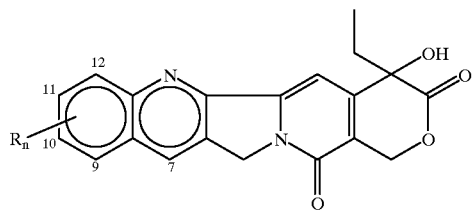

wherein ring a is substituted by $R_n$. Substituents include hydroxy, nitro, amino, chloro, bromo, iodo, fluoro, $C_{1-8}$ alkyl, $C_{1-8}$ alkoxy, trifluoromethyl, amino methyl, amido, hydrazino, azido, formyl, and cyano groups as well as groups comprising amino acids bonded to the A ring via the amino-nitrogen atom. Preferred alkyl groups include methyl, ethyl, propyl, butyl, isopropyl, isbutyl and secbutyl groups. Preferred alkoxy groups include methoxy, ethoxy, propoxy, and isopropoxy groups. Preferred amino acids are the the standard twenty amino acids. Two substituents on the a ring may be joined together to form a bifunction substituent. In addition, ring a may be modified to contain a hetero atom. Ring a may be a five or six carbon ring with an oxygen, nitrogen or sulphur.

The synthesis of camptothecin analogs with this formula can be carried out by those having ordinary skill in the art using synthesis schemes such as those that are described in U.S. Pat. Nos. 5,106,742, 5,122,526, 4,981,968, 5,180,722, 5,401,747, 5,227,380, 5,364,858, 5,244,903.

Example 8

Camptothecin analogs which have the formula as shown in Example 7 may be further substituted at the carbon on ring b ortho to the nitrogen on ring b. The position may substituted with a $C_{1-8}$ alkyl.

The synthesis of camptothecin analogs with this formula can be carried out by those having ordinary skill in the art using synthesis schemes such as those that are described in U.S. Pat. Nos. 5,122,606 and 5,053,512.

Example 9

Camptothecin analogs may have the formula:

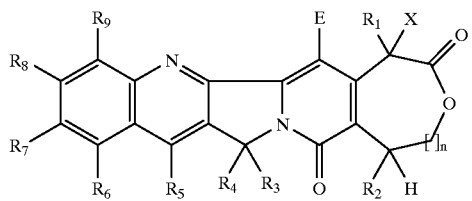

wherein:

E is H, $CO_2R$, $CONH_2$, CONHR, $CONR_2$, acyl, or CN;

X is H, OH, or OR;

$R_1$, $R_2$, $R_3$, and $R_4$ are independently the same or different and are H, or a linear or branched chain alkyl, alkylaryl, hydroxyalkyl group, or an aryl group, and $R_1$ may be allyl, propargyl or benzyl;

$R_5$, $R_6$, $R_7$, $R_8$, and $R_9$, are independently the same or different and are H, or a linear or branched chain alkyl, alkylaryl, alkoxy, hydroxyalkyl group, or aminoalkoxy group, or an aryl or aryloxy group, or an amino, lower acylamino, di(lower alkyl)amino group, or a C-glycal or hydroxyl, $CO_2R$, nitro, cyano, Cl, F, Br, I, $SR_{10}$, $NR_{11}R_{12}$ or $OR_{13}$, or $R_6$ is CHO, $CH_2R_{14}$ and $R_7$ is H, hydroxy, $-CH_2NH_2$ or formyl;

R is H, or a linear or branched alkyl, alkylaryl, or hydroxyalkyl group, or an aryl group, $R_{10}$, $R_{11}$, and $R_{12}$, are independently the same or different and are H, or a linear or branched chain alkyl, alkylaryl, hydroxyalkyl, or acyl group, or an aryl group;

$R_{13}$ is glycosyl;

$R_{14}$ is $OR_{15}$, $SR_{15}$, $CH_2NH_2$, cyano, $NR_{15}R_{16}$, or $N^+[R_{15}R_{16}R_{17}]$;

$R_{15}$, $R_{16}$ and $R_{17}$ are the same or different and are selected from H, $C_{1-6}$ alkyl, $C_{2-6}$ hydroxyalkyl, $C_{1-6}$ dialkylamino-$C_{2-6}$ alkyl, $C_{1-6}$ alkylamino-$C_{2-6}$ alkyl, $C_{2-6}$ aminoalkyl or a 3–7 member unsubstituted carbocyclic ring; and n is 0 or 1.

The synthesis of camptothecin analogs with this formula can be carried out by those having ordinary skill in the art using synthesis schemes such as those that are described in U.S. Pat. Nos. 5,391,745, 5,061,800, 5,004,758, 4,031,098, and 3,894,029.

Example 10

Camptothecin analogs may have the formula:

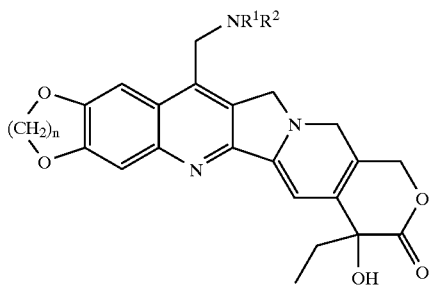

wherein:

n is 1 or 2;

$R_1$ is independently, H, lower alkyl, $(C_{3-7})$cycloalkyl lower alkyl, lower alkenyl, hydroxy lower alkyl, lower alkoxy lower alkyl; and $R_2$ is H or a pharmaceutically acceptable salt.

The synthesis of camptothecin analogs with this formula can be carried out by those having ordinary skill in the art using synthesis schemes such as those that are described in U.S. Pat. No. 5,342,947.

Example 11

Camptothecin analogs may have the formula:

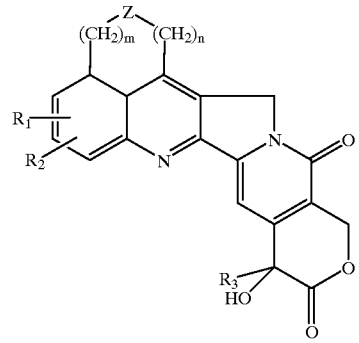

wherein:

n is 1 or 2;

$R_1$ and $R_2$ are, independently, hydrogen atoms, hydroxyl groups, $C_{1-6}$ alkyl groups, $C_{1-6}$ alkenyl groups, $C_{1-6}$ alkynyl groups, $C_{1-6}$ alkoxyl groups, $C_{1-6}$ aminoalkoxyl groups, halogen atoms, nitro groups, cyano groups, mercapto groups, $C_{1-6}$ alkylthio groups, $C_{1-6}$ hydroxyalkyl groups, $C_{1-6}$ halogenoalkyl groups, $C_{1-6}$ cyanoalkyl groups, $C_{1-6}$ nitroalkyl groups, amino groups which may contain protective groups, $C_{1-6}$ aminoalkyl groups which may contain protective groups or $C_{1-6}$ alkyl groups which may contain protective groups or $C_{1-6}$ alkyl groups, $C_{1-6}$ aminoalkylamino groups which may contain protective groups or $C_{1-6}$ alkyl groups at the amino-position, heterocyclic $C_{1-6}$ alkyl groups which may contain $C_{1-6}$ alkyl, $C_{1-6}$ alkoxyl, amino, halogeno, nitro, or cyano groups, heterocyclic $C_{1-6}$ alkylamino groups which may contain $C_{1-6}$ alkyl, $C_{1-6}$ alkoxyl, amino (which may contain protective groups), halogeno, nitro, cyano groups, or protective groups, amino-heterocyclic groups which may contain protective groups or $C_{1-6}$ alkyl groups at the nitrogen atom of the heterocyclic ring moiety or amino position, heterocyclic-amino groups which may contain protective groups of $C_{1-6}$ alkyl groups at the nitrogen atom of the heterocyclic ring moiety or amino position, carbamoyl groups which may contain protective groups or $C_{1-6}$ alkyl groups, heterocyclic carbonyl groups which may contain $C_{1-6}$ alkyl, $C_{1-6}$ alkoxyl, amino, hydroxyl, halogeno, nitro, or cyano groups;

$R_3$ represents an $C_{1-6}$ alkyl group;

Z represents O.S. $CH-R_4$ ($R_4$ stands for a hydrogen atom or a $C_{1-6}$ alkyl group), or $N-R_5$ ($R_5$ stands for a hydrogen atom, a $C_{1-6}$ alkyl group, or a protective group for the amino group); and m and n independently represent 0, 1 or 2 provided that m and n are not both equal to 2, and wherein said heterocyclic group is selected from the group consisting of azetidine, pyrrolidine, piperidine, piperazine, imidazoline, and morpholine, and wherein said protective group is selected from the group consisting of acetyl, formyl, trityl, terbutoxycarbonyl, and p-methoxybenzoyloxycarbonyl.

The synthesis of camptothecin analogs with this formula can be carried out by those having ordinary skill in the art using synthesis schemes such as those that are described in U.S. Pat. Nos. 4,939,255 and 5,062,795.

Example 12

Camptothecin analogs may have the formula:

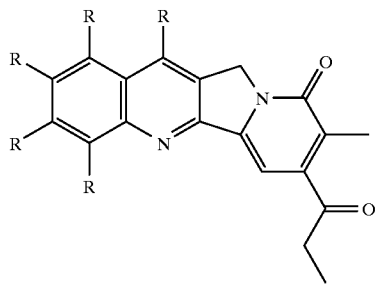

wherein the compound is 8-methyl-7-(1-oxopropyl) indolizino [1,2-b]quinolin-9(11H)-one or a substituted 8-methyl-7-(1-oxopropyl)indolizino [1,2-b]quinolin-9 (11H)-one.

The synthesis of camptothecin analogs with this formula can be carried out by those having ordinary skill in the art using synthesis schemes such as those that are described in U.S. Pat. No. 5,155,225.

Example 13

Camptothecin analogs may have the formula:

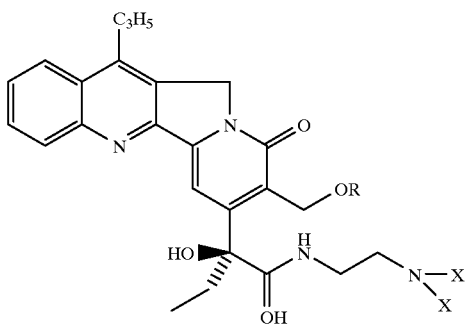

wherein:
X is a lower alkyl group; and
R is a hydrogen atom or the grouping —COY where Y is a linear or branched unsubstituted $C_1$–$C_1$ alkyl group, a lower alkyl group substituted by a halogen atom or a lower alkylthio, amino, acylamino, hydroxyl, lower alkoxy, arloxy or lower alkoxycarbonyl group; a $C_3$–$C_{19}$ alkenyl, $C_3$–$C_{19}$ alkynyl or $C_3$–$C_8$ cycloalkyl group; a $C_3$–$C_8$ cycloalkyl group substituted by an acylamino-lower alkyl group; an N-acylpyrrolidyl group, a phenyl group; a phenyl group substituted by a halogen atom or a trifluoromethyl, nitro, amino, lower alkoxycarbonyl, lower alkyl, phenyl or lower alkoxy; a cinnamyl group; a benzyl group; a naphthyl group; a pyridyl group; a furyl group; or a thienyl group, as well as acid addition salts and quaternary ammonium salts thereof.

The synthesis of camptothecin analogs with this formula can be carried out by those having ordinary skill in the art using synthesis schemes such as those that are described in U.S. Pat. No. 4,914,205.

---

We claim:

1. A method of identifying inhibitors of *C. albicans* topoisomerase I protein comprising the steps of:
   contacting a first host cell which is deficient in a functional topoisomerase gene except for a functional gene that encodes *C. albicans* topoisomerase I protein with a test compound;
   contacting a second host cell which is deficient in a functional topoisomerase gene except for a functional gene that encodes non-*C. albicans* topoisomerase I protein with a test compound;
   identifying a test compound whose presence results in the death of the first host cell but not the second host cell.

2. The method of claim 1 wherein said functional gene that encodes *C. albicans* topoisomerase I protein comprises SEQ ID NO:1.

3. A method of identifying inhibitors of *C. albicans* topoisomerase I protein comprising the steps of:
   contacting a first host cell which is deficient in a functional endogenous topoisomerase I gene with a test compound, wherein said first host organism is an organism other than *C. albicans* and comprises a functional gene that encodes *C. albicans* topoisomerase I protein;
   contacting a second host cell which comprises a functional topoisomerase I gene with a test compound wherein said second host organism is an organism other than *C. albicans* and is free of a functional gene that encodes *C. albicans* topoisomerase I protein;
   identifying a test compound whose presence results in the death of the first host cell but not the second host cell.

4. The method of claim 3 wherein said functional gene that encodes *C. albicans* topoisomerase I protein comprises SEQ ID NO:1.

5. The method of claim 3 wherein said second host cell comprises a functional endogenous topoisomerase I gene.

6. The method of claim 3 wherein said second host cell is deficient in a functional endogenous topoisomerase I gene and comprises a functional non-endogenous topoisomerase I gene.

7. The method of claim 3 wherein said second host cell is deficient in a functional endogenous topoisomerase I gene and comprises a functional human heterologous topoisomerase I gene.

8. The method of claim 3 wherein said first host cell and second host cell are cells of the species selected from the group consisting of Saccharomyces species, Schizosaccharomyces species, *Escherichia coli*, and *Salmonella typhimurium*.

9. The method of claim 3 wherein said first host cell and second host cell are yeast cells.

10. The method of claim 9 wherein said functional gene that encodes *C. albicans* topoisomerase I protein comprises SEQ ID NO:1.

11. The method of claim 9 wherein said second host cell comprises a functional endogenous topoisomerase I gene.

12. The method of claim 9 wherein said second host cell is deficient in a functional endogenous topoisomerase I gene and comprises a functional non-endogenous topoisomerase I gene.

13. The method of claim 9 wherein said second host cell is deficient in a functional endogenous topoisomerase I gene and comprises a functional human heterologous topoisomerase I gene.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 3143 base pairs
      (B) TYPE: nucleic acid
      (C) STRANDEDNESS: double
      (D) TOPOLOGY: unknown (ii) MOLECULE TYPE: genomic DNA (ix) FEATURE:
      (A) NAME/KEY: CDS
      (B) LOCATION: 547..2889

(xi) SEQUENCE DESCRIPTION: SEQ ID NO:1:

```
GAATTCCTCA AACACGGTCA AAAAAATACC AACTATCTTC TGTTTCTCCC CACTCACACG      60

ACCCAACTAT TTTTTTGGTG ATGGTTTTAG GCGCGACGTT AATCATTTTT ACTATTGAGA     120

ATGATTACTC CCACATTCTA TTACACCTCA TCTTCATCTT CATCTTTCAT CTTTCACATC     180

ACTAAATATA ACCTTGCGAC CTTCACAAAT TTTTTTTTTT GACAAGCAAT CCAAAATTAC     240
```

```
AATTTTCATT TCATTTCTTT TATATATAAA AGTTTTTCAC CATTAATTTC ACCACACATC      300

TCATTAGCAA TTGGGCAAAA ATAGAAAGTA ATTTTATAAC TTATAACCAA AAACAATTCA      360

AGAACAATAT CATTATTATT AAATTTATCA CGGAATTTGT TTTGCAAATC AAGTAAGAAC      420

AATTTCCATC AATTTACTCA TCAGTTTGGT TGTAATAATA AAAACAGATT ATTTTTCTTA      480

TCATCACCAC CAAGAGTATT CCGTTATTTA AATCCATTAT TTGTTCGTTC ATATAGCATA      540

ATTCCT ATG AGT TCA TCA GAC GAA GAA GAC ATT GCC TTG TCT AGA CTC         588
       Met Ser Ser Ser Asp Glu Glu Asp Ile Ala Leu Ser Arg Leu
        1               5                  10

GCT AAA AAA TCA TCC TCG ATC ACT TCA GCT TCC ACT TAT GAA GAC GAT        636
Ala Lys Lys Ser Ser Ser Ile Thr Ser Ala Ser Thr Tyr Glu Asp Asp
 15              20                  25                  30

GAA GAT GAT GAT ATC CCT TTA GCT AAA AAA TCC AGG AAA AAG AGG GTT        684
Glu Asp Asp Asp Ile Pro Leu Ala Lys Lys Ser Arg Lys Lys Arg Val
             35                  40                  45

GAA TCT GAT TAT GAA GAA GAT GAA GAC GAA GTC CCA TTG AAA AAG AGA        732
Glu Ser Asp Tyr Glu Glu Asp Glu Asp Glu Val Pro Leu Lys Lys Arg
         50                  55                  60

AAA TTG TCT AAT GGT AGA GCA AAA AAA CAA GTT AAA ACC GAA ACT AAA        780
Lys Leu Ser Asn Gly Arg Ala Lys Lys Gln Val Lys Thr Glu Thr Lys
         65                  70                  75

GTT AAA AAG GAA CCT AAA AGT GCC AAT AAA TCC AAA TCT ACA TCT AAA        828
Val Lys Lys Glu Pro Lys Ser Ala Asn Lys Ser Lys Ser Thr Ser Lys
 80                  85                  90

AAG GAC ACC AAA GTT AAG AAA GAG AAA ACT ACA GTC AAG AAG GAA TCT        876
Lys Asp Thr Lys Val Lys Lys Glu Lys Thr Thr Val Lys Lys Glu Ser
 95              100                 105                 110

AAA GCC ACA AGC ACT AAA GTG AAA GAA GAA TCC AAA ACT CAA TCA GAT        924
Lys Ala Thr Ser Thr Lys Val Lys Glu Glu Ser Lys Thr Gln Ser Asp
             115                 120                 125

TCA CAA GCA TCG GTT AAA TCT GAA ACT CCT GAA GAA GAT CAA GGG TAC        972
Ser Gln Ala Ser Val Lys Ser Glu Thr Pro Glu Glu Asp Gln Gly Tyr
             130                 135                 140

AAA TGG TGG GAA GTG AAT CAA GAA GAA GAA GGT GAT GGT TAT ATC AAA        1020
Lys Trp Trp Glu Val Asn Gln Glu Glu Glu Gly Asp Gly Tyr Ile Lys
         145                 150                 155

TGG CAA ACA CTA GAA CAT AAC GGT GTT ATG TTT CCA CCA CCA TAT GAA        1068
Trp Gln Thr Leu Glu His Asn Gly Val Met Phe Pro Pro Pro Tyr Glu
 160                 165                 170

CCA TTA CCA TCT CAT GTC AAA TTA TAT TAT AAC AAT AAA CCA GTT AAT        1116
Pro Leu Pro Ser His Val Lys Leu Tyr Tyr Asn Asn Lys Pro Val Asn
175                 180                 185                 190

TTA CCT CCA GAA GCA GAA GAA GTT GCC GGA TTT TAT GGA GCA ATG TTA        1164
Leu Pro Pro Glu Ala Glu Glu Val Ala Gly Phe Tyr Gly Ala Met Leu
             195                 200                 205

GAA ACT GAT CAT GCT AAA AAC CCA GTT TTC CAA AAG AAT TTT TTC AAT        1212
Glu Thr Asp His Ala Lys Asn Pro Val Phe Gln Lys Asn Phe Phe Asn
             210                 215                 220

GAT TTT TTG GAA GTT TTA AAA GAA TGT GGT GGT TGT GGT GTT GAA ATT        1260
Asp Phe Leu Glu Val Leu Lys Glu Cys Gly Gly Cys Gly Val Glu Ile
         225                 230                 235

AAA AAA TTT GAA AAA TTA GAT TTT AGT AAA ATG TAT GCT CAT TTT GAA        1308
Lys Lys Phe Glu Lys Leu Asp Phe Ser Lys Met Tyr Ala His Phe Glu
 240                 245                 250

AAA TTA CGT GAA GAG AAA AAG GCC ATG AGT AGG GAA GAA AAG AAA AGA        1356
Lys Leu Arg Glu Glu Lys Lys Ala Met Ser Arg Glu Glu Lys Lys Arg
 255                 260                 265                 270
```

| | | |
|---|---|---|
| ATC AAA GAA GAA AAA GAA AAA GAA GAA GAA CCT TAT AGG ACT TGT TAT<br>Ile Lys Glu Glu Lys Glu Lys Glu Glu Glu Pro Tyr Arg Thr Cys Tyr<br>275 280 285 | 1404 | |
| CTT AAT GGT AGA AAA GAA TTA GTG GGG AAT TTC CGT ATT GAA CCT CCA<br>Leu Asn Gly Arg Lys Glu Leu Val Gly Asn Phe Arg Ile Glu Pro Pro<br>290 295 300 | 1452 | |
| GGT TTA TTC CGT GGT CGT GGT GCA CAT CCT AAA ACT GGG AAA TTA AAA<br>Gly Leu Phe Arg Gly Arg Gly Ala His Pro Lys Thr Gly Lys Leu Lys<br>305 310 315 | 1500 | |
| CGT CGA GTA GTG CTG GAA CAA GTG ACT TTG AAT TTA GGT AAA GAT GCT<br>Arg Arg Val Val Leu Glu Gln Val Thr Leu Asn Leu Gly Lys Asp Ala<br>320 325 330 | 1548 | |
| AAA ATA CCT GAA CCA CCT GCA GGC CAT CAA TGG GGG GAA ATT AGA CAT<br>Lys Ile Pro Glu Pro Pro Ala Gly His Gln Trp Gly Glu Ile Arg His<br>335 340 345 350 | 1596 | |
| GAT AAT GAA GTC ACT TGG TTA GCC ATG TGG AAA GAA AAT ATT TCT GAT<br>Asp Asn Glu Val Thr Trp Leu Ala Met Trp Lys Glu Asn Ile Ser Asp<br>355 360 365 | 1644 | |
| TCA TTG AAA TAC GTT AGA TTT GCT AAT AAT TCT TCA GTT AAA GGT CAA<br>Ser Leu Lys Tyr Val Arg Phe Ala Asn Asn Ser Ser Val Lys Gly Gln<br>370 375 380 | 1692 | |
| TCC GAT TTC AAA AAA TTT GAA ACG GCG AGA AAA TTA AGA GAT CAC GTT<br>Ser Asp Phe Lys Lys Phe Glu Thr Ala Arg Lys Leu Arg Asp His Val<br>385 390 395 | 1740 | |
| GAT TCT ATT AGA AAA GAT TAT ACC AAA ATG TTA AAA TCA GAG AAA ATG<br>Asp Ser Ile Arg Lys Asp Tyr Thr Lys Met Leu Lys Ser Glu Lys Met<br>400 405 410 | 1788 | |
| CAA GAT AGA CAA ATG GCC ACG GCT ATG TAT CTT ATT GAT GTT TTT GCA<br>Gln Asp Arg Gln Met Ala Thr Ala Met Tyr Leu Ile Asp Val Phe Ala<br>415 420 425 430 | 1836 | |
| TTG AGG GCT GGT GGT GAA AAA GGT GAG GAT GAA GCC GAT ACC GTT GGT<br>Leu Arg Ala Gly Gly Glu Lys Gly Glu Asp Glu Ala Asp Thr Val Gly<br>435 440 445 | 1884 | |
| TGT TGT TCA TTA CGA TAT GAA CAT GTA ACT TTA AAA CCA CCC AAC AAG<br>Cys Cys Ser Leu Arg Tyr Glu His Val Thr Leu Lys Pro Pro Asn Lys<br>450 455 460 | 1932 | |
| GTT ATT TTC GAT TTT TTG GGT AAA GAT TCA ATT AGA TTT TAT CAA GAA<br>Val Ile Phe Asp Phe Leu Gly Lys Asp Ser Ile Arg Phe Tyr Gln Glu<br>465 470 475 | 1980 | |
| GTT GAA GTT GAT AAA CAA GTT TTC AAA AAT CTA CGA ATT TTC AAA AAA<br>Val Glu Val Asp Lys Gln Val Phe Lys Asn Leu Arg Ile Phe Lys Lys<br>480 485 490 | 2028 | |
| TCT CCT AAA CAA CCT GGT GAT GAT TTA TTT GAT CGT ATA AAC CCT TCA<br>Ser Pro Lys Gln Pro Gly Asp Asp Leu Phe Asp Arg Ile Asn Pro Ser<br>495 500 505 510 | 2076 | |
| TTA GTC AAT CGA CAA TTA CAA AAT TAT ATG AAA GGA TTA ACA GCA AAA<br>Leu Val Asn Arg Gln Leu Gln Asn Tyr Met Lys Gly Leu Thr Ala Lys<br>515 520 525 | 2124 | |
| GTT TTC CGT ACA TAT AAT GCC TCG AAA ACC ATG CAA GAT CAA ATT GAT<br>Val Phe Arg Thr Tyr Asn Ala Ser Lys Thr Met Gln Asp Gln Ile Asp<br>530 535 540 | 2172 | |
| ATA ATT GAA AAT GAA GGT ACA GTG GCG GAA AAA GTG GCT AAA TTC AAT<br>Ile Ile Glu Asn Glu Gly Thr Val Ala Glu Lys Val Ala Lys Phe Asn<br>545 550 555 | 2220 | |
| GCT GCC AAT AGA ACG GTG GCT ATT TTA TGT AAT CAC CAG CGT ACG GTC<br>Ala Ala Asn Arg Thr Val Ala Ile Leu Cys Asn His Gln Arg Thr Val<br>560 565 570 | 2268 | |
| AGT AAA ACC CAT GGT GAT AGT GTT CAG AGA ATT AAT GAC AAA TTG AAA<br>Ser Lys Thr His Gly Asp Ser Val Gln Arg Ile Asn Asp Lys Leu Lys<br>575 580 585 590 | 2316 | |

```
AAA TTC ATG TGG CAA AAG ATT AGA TTA AAG AAA ATG ATC TTA CAA TTA     2364
Lys Phe Met Trp Gln Lys Ile Arg Leu Lys Lys Met Ile Leu Gln Leu
                595                 600                 605

GAA CCC AAA TTG AAA AAG AAA GAT TCG AAA TAT TTT GAA GAA ATT GAT     2412
Glu Pro Lys Leu Lys Lys Lys Asp Ser Lys Tyr Phe Glu Glu Ile Asp
            610                 615                 620

GAT TTA CTC AAA GAA GAT ATT GAA CAT ATT CAT CAT ACT ATA ATT AAA     2460
Asp Leu Leu Lys Glu Asp Ile Glu His Ile His His Thr Ile Ile Lys
                625                 630                 635

AGA CAA CGA GAA CAA GCT AAA AAA AAA TTA GAA CGT GAT AAT GAA AAA     2508
Arg Gln Arg Glu Gln Ala Lys Lys Lys Leu Glu Arg Asp Asn Glu Lys
640                 645                 650

TTG AAA CTT GAA GGT AAA CCA TTA TTA ACT GAA TCA GAT ATA AAA GAT     2556
Leu Lys Leu Glu Gly Lys Pro Leu Leu Thr Glu Ser Asp Ile Lys Asp
655                 660                 665                 670

AAA TTA GAT AAA ATT GAT GAA TTA GAA AAA GAA TAT CAA AAA GAA TTG     2604
Lys Leu Asp Lys Ile Asp Glu Leu Glu Lys Glu Tyr Gln Lys Glu Leu
                675                 680                 685

AAA ACT GGT AAA CCA ATA GTC ACC AAA AAT GCT ACC GTT GAA AAA TTA     2652
Lys Thr Gly Lys Pro Ile Val Thr Lys Asn Ala Thr Val Glu Lys Leu
                690                 695                 700

AAA CAA CAA ATT GAA ACT CTT GAA AAT AAA ATT CTT AAT GTT TCA ATT     2700
Lys Gln Gln Ile Glu Thr Leu Glu Asn Lys Ile Leu Asn Val Ser Ile
                705                 710                 715

CAA TTA AAA GAT AAA GAA GAT AAT TCT GAA GTT TCT TTA GGA ACT TCA     2748
Gln Leu Lys Asp Lys Glu Asp Asn Ser Glu Val Ser Leu Gly Thr Ser
720                 725                 730

AAA ATG AAT TAT ATT GAT CCA AGA TTA ATT GTT ATG TTT TCT AAA AAA     2796
Lys Met Asn Tyr Ile Asp Pro Arg Leu Ile Val Met Phe Ser Lys Lys
735                 740                 745                 750

TTT GAT GTT CCT ATT GAA AAA TTA TTT ACC AAA ACT TTA AGA GAA AAG     2844
Phe Asp Val Pro Ile Glu Lys Leu Phe Thr Lys Thr Leu Arg Glu Lys
                755                 760                 765

TTC ATT TGG GCT ATT GAA TCA GCT GAT GAA AAT TGG AGA TTC TAA         2889
Phe Ile Trp Ala Ile Glu Ser Ala Asp Glu Asn Trp Arg Phe *
                770                 775                 780

AATTAGGGGT TGTTTCTTA GCTTATTATT ATATACTATA TGCTGTAGAG TAAAATTTTG    2949

TACCTTGTAA TATATATATA TACATTGTTT CAACATAGAA AAATAGATTG ATACTGCAGT   3009

ATGAAAAAGA ATATGCACAC ACCAAGCAAG TGTATTTTAG ATAAAGGATT GGTGTTTTGA   3069

TATTGGAAGG GTGAAAGATG AAGGGGGTAT CACACAGACA CGTACAATCA AGAAATTGAA   3129

ATTTCTCCGA ATTC                                                    3143

(2) INFORMATION FOR SEQ ID NO:2:

(i) SEQUENCE CHARACTERISTICS:
        (A) LENGTH:  780 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Ser Ser Asp Glu Glu Asp Ile Ala Leu Ser Arg Leu Ala Lys
  1               5                  10                  15

Lys Ser Ser Ser Ile Thr Ser Ala Ser Thr Tyr Glu Asp Asp Glu Asp
                 20                  25                  30

Asp Asp Ile Pro Leu Ala Lys Lys Ser Arg Lys Lys Arg Val Glu Ser
             35                  40                  45
```

```
Asp Tyr Glu Glu Asp Glu Asp Glu Val Pro Leu Lys Lys Arg Lys Leu
     50                  55                  60
Ser Asn Gly Arg Ala Lys Lys Gln Val Lys Thr Glu Thr Lys Val Lys
 65                  70                  75                  80
Lys Glu Pro Lys Ser Ala Asn Lys Ser Lys Ser Thr Ser Lys Lys Asp
                 85                  90                  95
Thr Lys Val Lys Lys Glu Lys Thr Thr Val Lys Lys Glu Ser Lys Ala
            100                 105                 110
Thr Ser Thr Lys Val Lys Glu Glu Ser Lys Thr Gln Ser Asp Ser Gln
        115                 120                 125
Ala Ser Val Lys Ser Glu Thr Pro Glu Glu Asp Gln Gly Tyr Lys Trp
    130                 135                 140
Trp Glu Val Asn Gln Glu Glu Gly Asp Gly Tyr Ile Lys Trp Gln
145                 150                 155                 160
Thr Leu Glu His Asn Gly Val Met Phe Pro Pro Tyr Glu Pro Leu
                165                 170                 175
Pro Ser His Val Lys Leu Tyr Tyr Asn Asn Lys Pro Val Asn Leu Pro
                180                 185                 190
Pro Glu Ala Glu Glu Val Ala Gly Phe Tyr Gly Ala Met Leu Glu Thr
                195                 200                 205
Asp His Ala Lys Asn Pro Val Phe Gln Lys Asn Phe Asn Asp Phe
        210                 215                 220
Leu Glu Val Leu Lys Glu Cys Gly Gly Cys Gly Val Glu Ile Lys Lys
225                 230                 235                 240
Phe Glu Lys Leu Asp Phe Ser Lys Met Tyr Ala His Phe Glu Lys Leu
                245                 250                 255
Arg Glu Glu Lys Lys Ala Met Ser Arg Glu Lys Lys Arg Ile Lys
                260                 265                 270
Glu Glu Lys Glu Lys Glu Glu Pro Tyr Arg Thr Cys Tyr Leu Asn
        275                 280                 285
Gly Arg Lys Glu Leu Val Gly Asn Phe Arg Ile Glu Pro Pro Gly Leu
    290                 295                 300
Phe Arg Gly Arg Gly Ala His Pro Lys Thr Gly Lys Leu Lys Arg Arg
305                 310                 315                 320
Val Val Leu Glu Gln Val Thr Leu Asn Leu Gly Lys Asp Ala Lys Ile
                325                 330                 335
Pro Glu Pro Pro Ala Gly His Gln Trp Gly Glu Ile Arg His Asp Asn
                340                 345                 350
Glu Val Thr Trp Leu Ala Met Trp Lys Glu Asn Ile Ser Asp Ser Leu
            355                 360                 365
Lys Tyr Val Arg Phe Ala Asn Asn Ser Ser Val Lys Gly Gln Ser Asp
        370                 375                 380
Phe Lys Lys Phe Glu Thr Ala Arg Lys Leu Arg Asp His Val Asp Ser
385                 390                 395                 400
Ile Arg Lys Asp Tyr Thr Lys Met Leu Lys Ser Glu Lys Met Gln Asp
                405                 410                 415
Arg Gln Met Ala Thr Ala Met Tyr Leu Ile Asp Val Phe Ala Leu Arg
            420                 425                 430
Ala Gly Gly Glu Lys Gly Glu Asp Glu Ala Asp Thr Val Gly Cys Cys
        435                 440                 445
Ser Leu Arg Tyr Glu His Val Thr Leu Lys Pro Pro Asn Lys Val Ile
    450                 455                 460
Phe Asp Phe Leu Gly Lys Asp Ser Ile Arg Phe Tyr Gln Glu Val Glu
465                 470                 475                 480
```

-continued

```
Val Asp Lys Gln Val Phe Lys Asn Leu Arg Ile Phe Lys Lys Ser Pro
                485                 490                 495

Lys Gln Pro Gly Asp Asp Leu Phe Asp Arg Ile Asn Pro Ser Leu Val
            500                 505                 510

Asn Arg Gln Leu Gln Asn Tyr Met Lys Gly Leu Thr Ala Lys Val Phe
            515                 520                 525

Arg Thr Tyr Asn Ala Ser Lys Thr Met Gln Asp Gln Ile Asp Ile Ile
        530                 535                 540

Glu Asn Glu Gly Thr Val Ala Glu Lys Val Ala Lys Phe Asn Ala Ala
545                 550                 555                 560

Asn Arg Thr Val Ala Ile Leu Cys Asn His Gln Arg Thr Val Ser Lys
                565                 570                 575

Thr His Gly Asp Ser Val Gln Arg Ile Asn Asp Lys Leu Lys Lys Phe
            580                 585                 590

Met Trp Gln Lys Ile Arg Leu Lys Lys Met Ile Leu Gln Leu Glu Pro
            595                 600                 605

Lys Leu Lys Lys Lys Asp Ser Lys Tyr Phe Glu Glu Ile Asp Asp Leu
        610                 615                 620

Leu Lys Glu Asp Ile Glu His Ile His His Thr Ile Ile Lys Arg Gln
625                 630                 635                 640

Arg Glu Gln Ala Lys Lys Lys Leu Glu Arg Asp Asn Glu Lys Leu Lys
                645                 650                 655

Leu Glu Gly Lys Pro Leu Leu Thr Glu Ser Asp Ile Lys Asp Lys Leu
            660                 665                 670

Asp Lys Ile Asp Glu Leu Glu Lys Glu Tyr Gln Lys Glu Leu Lys Thr
            675                 680                 685

Gly Lys Pro Ile Val Thr Lys Asn Ala Thr Val Glu Lys Leu Lys Gln
        690                 695                 700

Gln Ile Glu Thr Leu Glu Asn Lys Ile Leu Asn Val Ser Ile Gln Leu
705                 710                 715                 720

Lys Asp Lys Glu Asp Asn Ser Glu Val Ser Leu Gly Thr Ser Lys Met
                725                 730                 735

Asn Tyr Ile Asp Pro Arg Leu Ile Val Met Phe Ser Lys Lys Phe Asp
            740                 745                 750

Val Pro Ile Glu Lys Leu Phe Thr Lys Thr Leu Arg Glu Lys Phe Ile
        755                 760                 765

Trp Ala Ile Glu Ser Ala Asp Glu Asn Trp Arg Phe
770                 775                 780
```